(12) United States Patent
Buckman et al.

(10) Patent No.: US 6,998,510 B2
(45) Date of Patent: Feb. 14, 2006

(54) METHOD AND APPARATUS FOR IMPROVED HEMOSTASIS AND DAMAGE CONTROL OPERATIONS

(75) Inventors: Robert F. Buckman, Radnor, PA (US); Jay A. Lenker, Laguna Beach, CA (US)

(73) Assignee: Damage Control Surgical Technologies, Inc., Laguna Beach, CA (US)

( * ) Notice: Subject to any disclaimer, the term of this patent is extended or adjusted under 35 U.S.C. 154(b) by 258 days.

(21) Appl. No.: 10/358,881

(22) Filed: Feb. 4, 2003

(65) Prior Publication Data

US 2003/0176828 A1 Sep. 18, 2003

Related U.S. Application Data

(60) Provisional application No. 60/424,038, filed on Nov. 5, 2002, and provisional application No. 60/354,429, filed on Feb. 4, 2002.

(51) Int. Cl.
*A61F 13/00* (2006.01)
*A61F 13/15* (2006.01)

(52) U.S. Cl. .................... 602/48; 604/358; 424/443
(58) Field of Classification Search ............ 602/41–43, 602/48; 604/358, 304–308, 1, 11; 424/443–449; 428/48; 528/386, 385
See application file for complete search history.

(56) References Cited

U.S. PATENT DOCUMENTS

| | | | | |
|---|---|---|---|---|
| 4,462,224 A | * | 7/1984 | Dunshee et al. | 62/530 |
| 4,538,603 A | * | 9/1985 | Pawelchak et al. | 602/56 |
| 4,541,426 A | * | 9/1985 | Webster | 602/47 |
| 4,728,642 A | * | 3/1988 | Pawelchak et al. | 514/57 |
| 4,733,659 A | | 3/1988 | Edenbaum et al. | 128/156 |
| 5,000,746 A | * | 3/1991 | Meiss | 604/304 |
| 5,016,629 A | * | 5/1991 | Kanare | 607/114 |
| 5,336,163 A | * | 8/1994 | DeMane et al. | 602/46 |
| 5,409,472 A | * | 4/1995 | Rawlings et al. | 604/307 |
| 5,423,736 A | * | 6/1995 | Cartmell et al. | 602/42 |
| 5,447,499 A | * | 9/1995 | Allaire et al. | 602/42 |
| 5,447,505 A | * | 9/1995 | Valentine et al. | 604/304 |
| 5,466,231 A | * | 11/1995 | Cercone et al. | 604/369 |
| 5,470,625 A | * | 11/1995 | Perrault | 428/48 |
| 5,478,308 A | * | 12/1995 | Cartmell et al. | 602/57 |
| 5,643,596 A | | 7/1997 | Pruss et al. | 424/426 |
| 5,763,411 A | | 6/1998 | Edwardson et al. | 514/21 |
| 5,800,372 A | | 9/1998 | Bell et al. | 602/48 |
| 5,823,984 A | * | 10/1998 | Silverberg | 602/61 |
| 5,843,060 A | * | 12/1998 | Cercone | 604/369 |
| 5,899,871 A | * | 5/1999 | Cartmell et al. | 602/43 |
| 6,054,122 A | | 4/2000 | MacPhee et al. | 424/94.4 |
| 6,056,970 A | | 5/2000 | Greenawalt et al. | 424/426 |
| 6,114,594 A | * | 9/2000 | Barikosky | 604/367 |
| 6,191,341 B1 | * | 2/2001 | Shippert | 604/383 |
| 6,768,040 B1 | * | 7/2004 | Sessions et al. | 602/56 |
| 2003/0093075 A1 | * | 5/2003 | Levinson | 606/54 |
| 2004/0064132 A1 | * | 4/2004 | Boehringer et al. | 604/543 |

FOREIGN PATENT DOCUMENTS

| | | |
|---|---|---|
| WO | WO 00/25726 | 5/2000 |
| WO | WO 2004062704 A1 * | 7/2004 |
| WO | WO 2004080498 A1 * | 9/2004 |

\* cited by examiner

*Primary Examiner*—Kim M. Lewis
(74) *Attorney, Agent, or Firm*—Crockett & Crockett; K. David Crockett, Esq.

(57) ABSTRACT

Devices and methods are disclosed for achieving hemostasis in traumatized patients. The devices utilize fluid impermeable outer surfaces and distributed pressure to achieve tamponade and hemostasis, primarily by exertion of pressure. The devices are capable of serving as carriers for throabogenic or antipathogenic agents. Peripheral haemostatic packing devices include optional adhesive hemostatic barriers to cover the entire wound area over the hemostatic pack. The hemostatic packing devices may be placed and removed by open surgery or laparoscopic access without generating excessive re-bleeding, and may further comprise antimicrobial or thrombogenic regions.

11 Claims, 9 Drawing Sheets

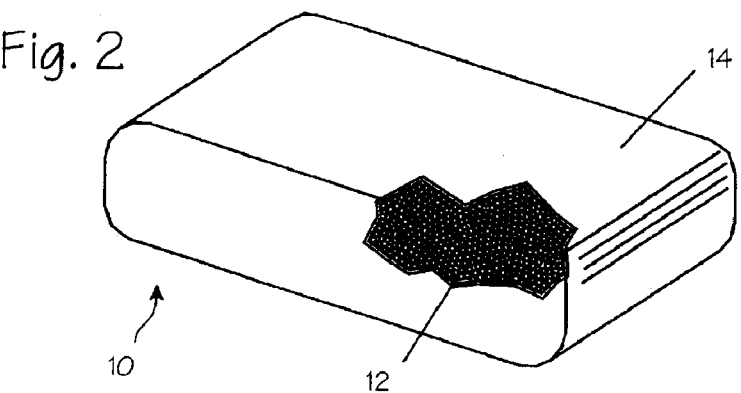
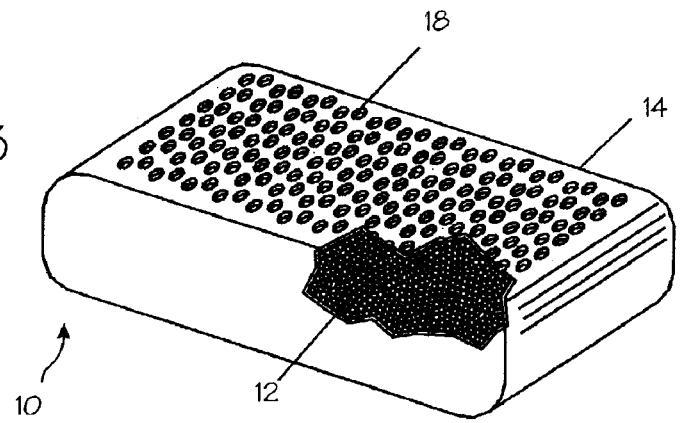
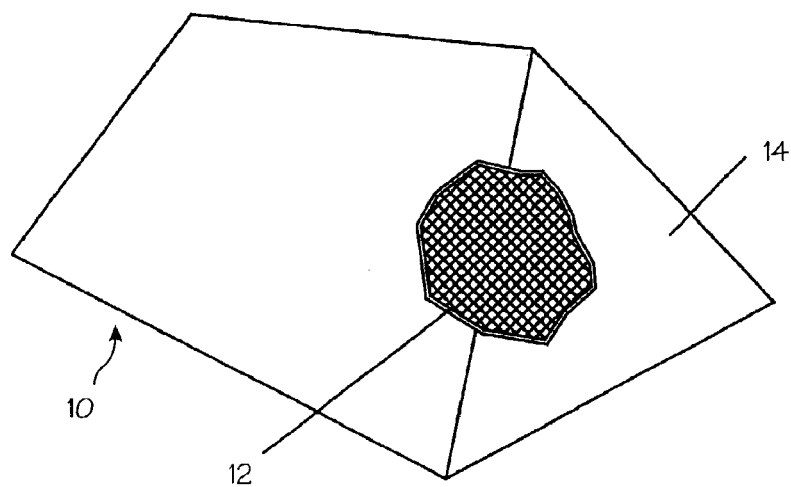

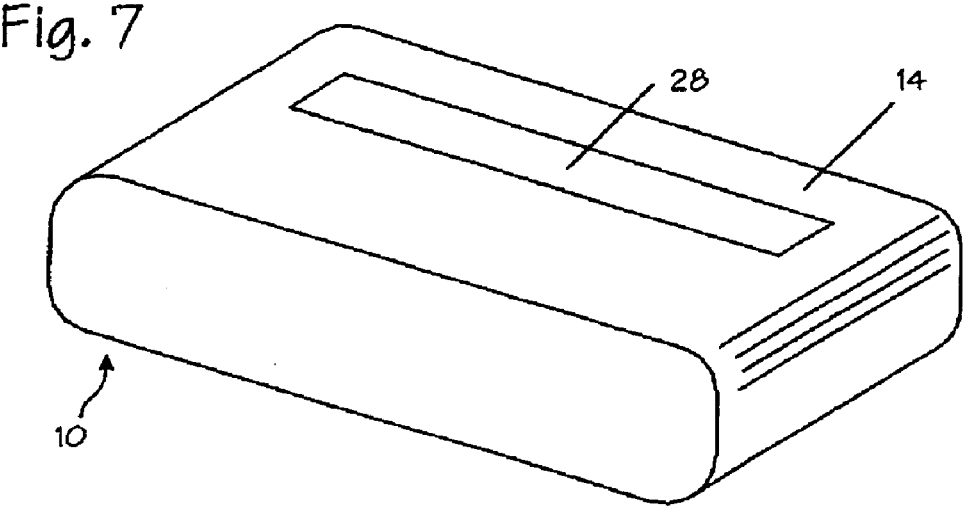
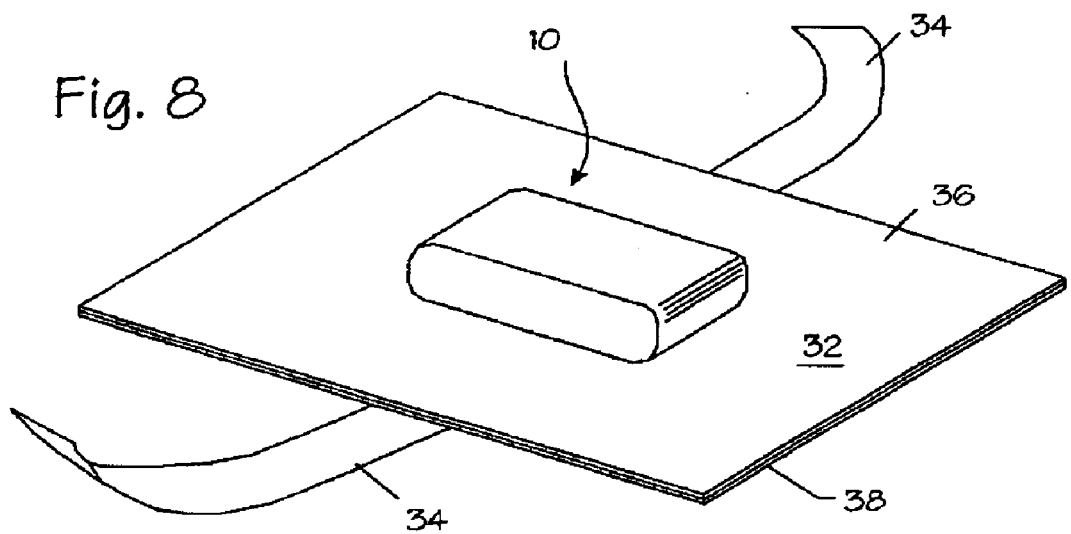

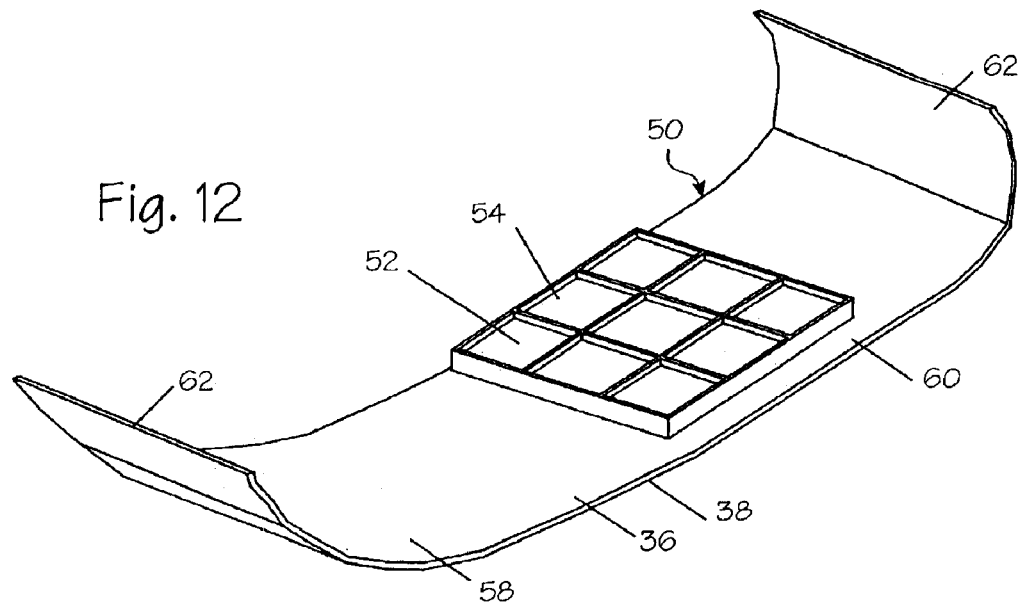
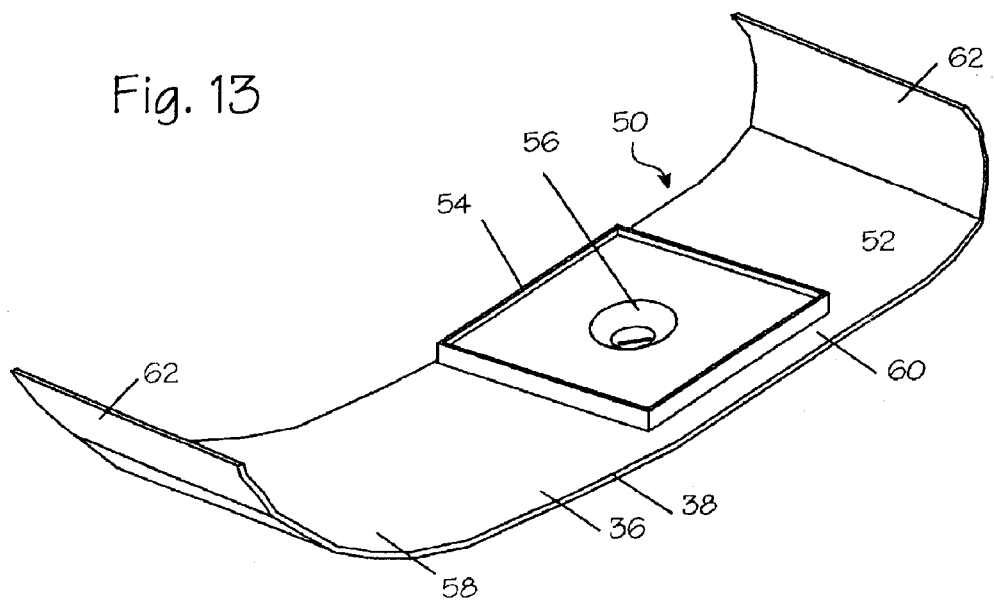

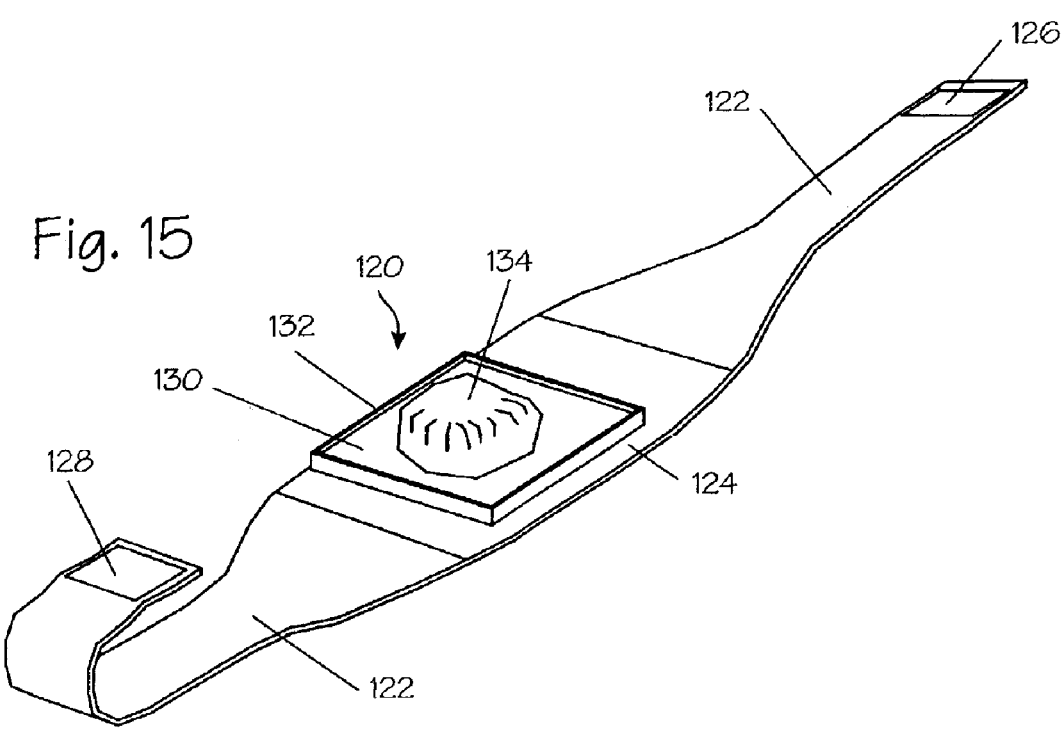

METHOD AND APPARATUS FOR IMPROVED HEMOSTASIS AND DAMAGE CONTROL OPERATIONS

The present application claims priority benefit under 35 USC § 119(e) from U.S. Provisional Application No. 60/354,429 filed Feb. 4, 2002, entitled "METHOD AND APPARATUS FOR IMPROVED HEMOSTASIS AND DAMAGE CONTROL OPERATIONS" and U.S. Provisional Application No. 60/424,038 filed Nov. 5, 2002, entitled METHOD AND APPARATUS FOR EMERGENCY VESSEL ANASTOMOSES, both of which are herein incorporated by reference.

FIELD OF THE INVENTION

The field of this invention is wound care during trauma surgery, general surgery, combat medicine, and emergency medical services.

BACKGROUND OF THE INVENTION

As recently as the early 1990s, surgical operations for trauma were directed at the anatomic repair of all injuries at time of the initial operation. It was observed during these exercises that many patients became hypothermic, acidotic, and coagulopathic. Patients showing these three signs often died. Death often occurred in the operating room due to exsanguinations, or postoperatively, due to the complications of prolonged shock and massive transfusion to replace blood lost as a result of the trauma.

One of the most notable developments in the recent evolution of surgery has been the introduction of the concept of staged laparotomy to overcome the deficiencies of the repair all-at-once approach. This new strategy of staged laparotomy, employing new tactics that have been termed damage control, is now used in 10% to 20% of all trauma laparotomies.

Ever since the advent of abdominal surgery, surgeons have relied on the same thinly woven cotton gauze packing pads that are currently in favor. These gauze pads are called laparotomy pads or Mickulitz pads. These pads were designed for use as sponges but not for use as hemostatic tampons. Nonetheless, since World War I, surgeons faced with severe bleeding have relied on packing patients with these sterilizable gauze sponges in an effort to control bleeding. Since World War II, it has been known that abdominal packing using these pads has been associated with abdominal sepsis and re-bleeding after pad removal. Despite these limitations, even today, they are the mainstay of damage control hemostasis.

The specific issues with the gauze pads are that they are porous and allow the free passage of blood through the mesh. Other unfavorable characteristics include the lack of intrinsic coagulation inducing properties. The pads are easily saturated but these pads do not stick to one another. The pads are capable of promoting infection because they serve as a nidus for bacteria in a contaminated field. They have no intrinsic antiseptic or antimicrobial action. These pads are unsuitable for packing solid viscera because they stick to the visceral wound tissue and cause re-bleeding upon removal. Although generally recognized as sub-optimal, the gauze pads have the advantages of being cheap, familiar and ubiquitous. For these later reasons, they continue to remain the mainstay of damage control hemostasis. Among the opportunities for new technologies and instruments to support the process of damage control, the first requirement is an improvement in the surgical pack.

Other current pads for hemostasis include gel-foam, Surgicel, and fibrin sponges. These devices are all liquid permeable and require blood coagulation to occur before impermeability and hemostasis are achieved. In addition, the fibrin sponges are very rigid and will not conform to a wound while in the dry state. Typical examples of the prior art in hemostatic packing systems include U.S. Pat. No. 5,643,596 to Pruss et al., U.S. Pat. No. 5,763,411 to Edwardson et al., U.S. Pat. No. 5,800,372 to Bell et al., U.S. Pat. No. 6,054,122 to MacPhee et al., and U.S. Pat. No. 6,056,970 to Greenawalt et al. These patents, all of which are included herein by reference, disclose permeable hemostatic packing and dressings with topical hemostatic coatings. These devices all serve the purpose of stopping bleeding in underlying vessels with an occlusive backing but the backing is still permeable to blood leakage. The lack of impermeability in these prior art patents is not recognized as an issue.

While hemostatic packing devices are well known in the art, the utility of said packing devices is limited by their propensity to harbor pathogens and their propensity to create re-bleeding by adherence to healing surfaces.

New devices, procedures and methods are needed to support the strategy of damage control in patients who have experienced massive bodily injury. Such devices and procedures are particularly important in the emergency, military, and trauma care setting. These new devices rely on the principles of impermeability to blood passage, limited nidus formation for bacteria, the ability to carry pro-thrombogenic material, and the lack of intrinsic thrombogenicity except by providing a physical barrier or pressure source.

SUMMARY OF THE INVENTION

The devices and methods described below provide for improved hemostatic packing in trauma care. The devices comprise impermeable barrier packs with various features provided to improved hemostasis, improved packing and placement of the packs, and easier removal of the pack after hemostasis is achieved. Other features of the pack include foldability and moldability to the anatomical surface. The exterior surface of the pack is not intrinsically thrombogenic but is capable of serving as a carrier for thrombogenic substances. Certain regions of the exterior surface of the pack may optionally comprise thrombogenic properties. The pack may be made with a plurality of surfaces, each with distinct characteristics. An exemplary version of the pack has a thin layer of polyethylene or polypropylene, which is impermeable to liquids, as its entire outer surface. A key advantage of the present invention, in its wet or dry state, is moldability, flexibility and shapability to the anatomical contacting surface, including the ability to pack wounds in solid viscera. The pack is able to distribute pressure within the wound to generate pressure tamponade. The pack is capable of generating pressure tamponade without regions of sharp or high stress such as would be generated by a rigid packing system. This improvement over certain very hard packing devices allows for better fit to the anatomy and the immediate formation of an impermeable barrier without the need to wait for blood coagulation to occur to form the hemostatic barrier. The hemostatic pack of the present invention is placed via open surgery or through laparoscopic instrumentation. The laparoscopic embodiment includes the capability of reversibly or irreversibly achieving a size and mass change in the device once it is placed within the patient.

The present invention distinguishes over the cited prior art because it requires no thrombogenic coatings, although it is capable of trapping and carrying such pro-thrombogenic coatings on its surface. The outer surface of the haemostatic packing sponge serves as a carrier by incorporating indents or villi to physically hold the pharmacological, thrombogenic or antibacterial coatings. Since the surface is impermeable to liquids, the arrest of hemorrhage is immediate and does not require thrombosis to occur. When the packing device of the present invention is removed from the patient, re-bleeding does not occur because there is no penetration of the wound tissues or clot into the interstices of the pack. An additional advantage of the impermeable pack is a resistance to bacteria and other pathogenic penetration.

In another embodiment of the invention, the pack comprises raised ridges or dams on its surface. These ridges or dams are comprised of soft conformable materials that form an edge seal to prevent the escape of blood from a wound. The pack optionally comprises additional regions or borders of enhanced blood clotting or thrombogenesis to assist with the hemostatic properties of the device.

In yet another embodiment of the present invention, the hemostatic pack comprises adhesives, fasteners, or the like to allow the packs to adhere to each other, thus forming a syncytium, or contiguous barrier comprised of more than one component, to prevent blood from escaping from a wound.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

FIG. 2 illustrates a hemostatic packing device comprising a closed-cell foam that is impermeable on both sides;

FIG. 3 illustrates a hemostatic packing device comprising an outer surface that is impermeable on both sides where the upper surface further comprises indentations capable of carrying exogenous thrombogenic substances;

FIG. 4 illustrates a hemostatic packing device comprising a polygonal deformable solid with an impermeable outer surface;

FIG. 7 illustrates a hemostatic packing device comprising an adhesive on at least a portion of the outer impermeable surface of said hemostatic packing device;

FIG. 8 illustrates a hemostatic packing device comprising a packing material with an impermeable outer surface affixed to an adhesive impermeable drape;

FIG. 12 illustrates a wound dressing or bandage for treating a wound to the arm or the leg comprising a series of blood dams.

FIG. 13 illustrates a wound dressing or bandage for treating a wound to the arm or the leg comprising a blood dam with a communicating valve;

FIG. 14A illustrates a lateral sectional view of two internal hemostatic packs for solid organs, viscera, and the like;

FIG. 15 illustrates an oblique view of a preferred wound dressing or bandage for treating a wound to a body part comprising a strap, a blood dam, and a pillow pack.

DETAILED DESCRIPTION OF THE INVENTION

Figure 1A:
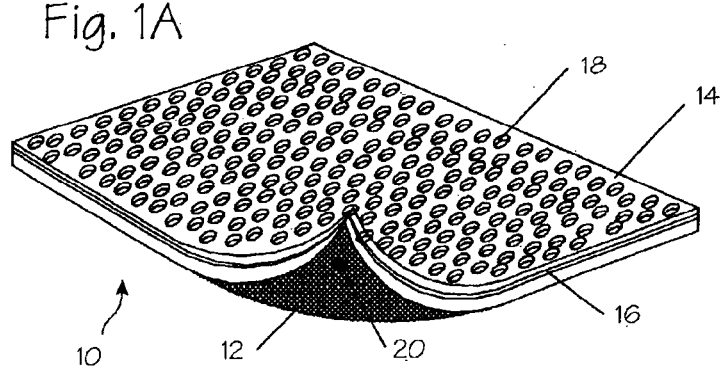
FIG. 1A illustrates a two-sided hemostatic pack comprising a sheet of material that is impermeable to liquid on one side and the other side is a permeable fabric affixed to the impermeable barrier.

FIG. 1A illustrates a diagram of a two-sided hemostatic packing device 10 of the present invention. The two-sided packing device 10 comprises a blood permeable layer or substrate 12 and a fluid impermeable covering 14. The fluid impermeable sheet 14 further comprises an optional adhesive layer 16, and a plurality of optional indentations 18 on the exterior surface. The fluid impermeable covering 14 or the substrate 12 may optionally comprise a plurality of radiopaque markers 20. The hemostatic packing device 10 is a flat sheet that is flexible and deformable. The substrate 12 is a flat sheet configuration and is integral to or affixed to the fluid impermeable covering 14. The fluid impermeable covering 14 optionally comprises a plurality of indentations 18. The radiopaque markers 20 may be wire form, dots or patches of barium-impregnated fabrics.

The substrate 12 is soft in its wet or dry state and may be bent, molded or deformed to maximize surface contact and force distribution on injured tissue. The substrate 12 is fabricated from cotton gauze, open or closed cell foam, sponge, fluids, particulates and the like, or from inflatable or packable masses of particulates. The foam configuration of the substrate 12 may be fabricated from materials such as polypropylene, polyvinyl chloride, polyurethane, polyethylene, silicone rubber, poly methyl methacrylate, polyvinyl alcohol and the like. The particulates of the inflatable embodiment of substrate 12 may be beads of collagen, PTFE, silica and the like. The fluid impermeable covering 14 is fabricated from materials such as polypropylene, polyvinyl chloride, polyurethane, polyethylene, silicone rubber, poly methyl methacrylate, polyvinyl alcohol, Tyvsk® and the like. The fluid impermeable covering 14 may also be fabricated from materials such as paper or cloth that is then coated or sprayed with impermeable materials such as polyethylene, polypropylene and the like. The use of rip-stop fabrics will help prevent tearing of the fluid impermeable covering 14.

The hemostatic packing device 10 is fabricated in a variety of sizes and thicknesses. The thickness varies from 0.1 mm to 50 mm. The length and width each may vary from 5 mm to 500 mm. The geometry is generally rectangular but may have triangular, circular, or polygonal configurations. The corners may be square or rounded.

The radiopaque markers 20 are fabricated from a group of materials including but not limited to barium impregnated fabrics or polymers, metal wires, and metal solids. Typical metals used for radiopacity include tantalum, platinum, gold, and the like.

The hemostatic packing device 10 is packaged in a sealed, sterile barrier package and is sterilized using standard techniques such as steam, cobalt radiation, ethylene oxide, electron beam and the like.

Figure 1B:
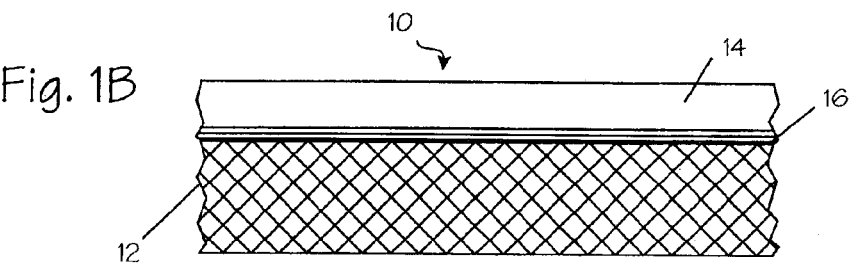
FIG. 1B illustrates a cross-sectional view of the two-sided haemostatic pack.

Referring to FIG. 1B, the hemostatic packing device 10 is shown from the side. The substrate 12, the fluid impermeable covering 14, and the adhesive layer 16 are clearly visible in this view.

Figure 1C:
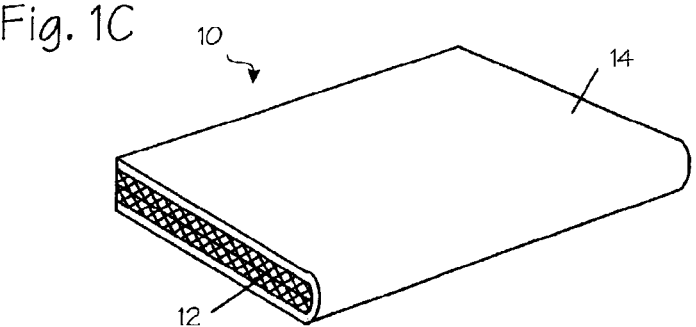
FIG. 1C illustrates the two-sided hemostatic packing device folded with the impermeable surface facing outward toward the wound surface.
Figure 1D:
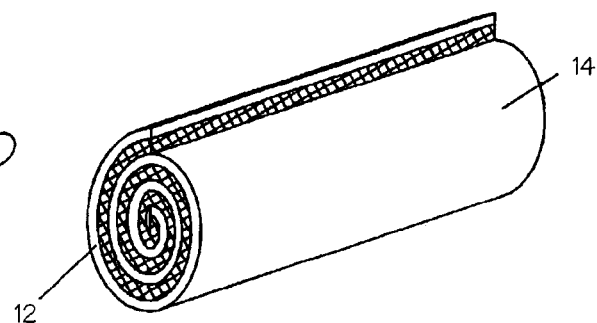
FIG. 1D illustrates the two-sided hemostatic pack rolled with the impermeable side out.

The component illustrated in FIGS. 1A and 1C are folded or rolled to form the desired hemostatic packs, which are illustrated in FIGS. 1C and 1D. FIG. 1C illustrates one embodiment of the hemostatic packing device 10 that is folded with the fluid impermeable covering 14 facing outward in preparation for use. FIG. 1D illustrates another embodiment of the hemostatic packing device 10 that is rolled with the fluid impermeable covering 14 facing outward in preparation for use. Prior to use (either in manufacture or in the field, immediately before packing a wound), the component sheet is folded or rolled. If folded or rolled in manufacture, the device will be packaged and shipped in its final form. If manufactured in the field, the doctor or paramedic will make the device from the component sheets, folding or rolling the sheets to make packs of suitable size and shape, as dictated by the shape of the wound presented.

FIG. 2 illustrates another embodiment of the haemostatic packing device 10 where the substrate 12 and the fluid impermeable covering 14 are fabricated from the same material. In this embodiment, the hemostatic packing device 10 is fabricated from closed-cell foam, where the substrate is the foam, and the outer layer is the typically impermeable skin of the foam. The foam material allows for a resilient, deformable substrate while maintaining the fluid impermeable covering 14 that is impermeable to fluid penetration since it is a closed cell structure.

FIG. 3 illustrates the hemostatic packing device 10 where the upper side of the fluid impermeable covering 14 comprises indentations 18, that may be in the form of dimpling or waffling of varying depth that are useful to deliver thrombogenic, pharmaceutical or antibacterial agents. The indentations 18 are formed using molds wherein the outer surface of the fluid impermeable covering 14 of the closed-cell substrate 12 is formed against the mold. In another embodiment, the indents 18 are formed by impressing the fluid impermeable outer sheet with a mold or other forming device. In yet another embodiment, the the fluid impermeable covering 14 comprises projections, or villi, that serve to trap and carry the pharmaceutical, antibacterial or thrombogenic agents. The projections or indents may be macroscopic or microscopic.

FIG. 4 illustrates another embodiment of the haemostatic packing device 10 wherein the substrate 12 forms a polygonal solid. The polygonal solids include shapes such as brick or rectangular solid, waffle, pyramid, sheet, and oval. The polygonal solids also include extruded shapes such as cylinders, or extended lengths of cross-sections such as rectangular, oval, circular, trapezoidal, triangular, etc. The lengths of these devices range from 5 mm to 1000 mm. The width dimensions of these devices range from 1 mm to 200 mm. For a typical use, such as v-shaped wounds such as laceration in the leg, the device can be provided in dimensions of about three to eight inches long (7.5 to 20 cm), with sides of about 0.5 to 2 inches (1 to 5 cm). At least part of the fluid impermeable covering 14 of the hemostatic packing device 10 comprises a fluid impermeable barrier. This fluid impermeable covering 14 may be smooth, indented, or covered by villi, or projections. The substrate 12 is fabricated from materials that allow for deformation in the dry or wet state. These materials include cotton batting, polymeric foams of varying densities, sand, polymer beads, oils including silicone oils, water, and the like.

Referring to FIGS. 1A, 1B, 1C, 1D, 2, 3, and 4, the hemostatic packing device 10, in another embodiment, comprises a fluid fluid impermeable covering 14 that is fabricated from resorbable materials. The substrate 12 may be removed and the fluid impermeable covering 14 left behind to complete healing. The 14 is fabricated from resorbable materials such as polyglycolic acid (PGPL), polylactic acid (PLA) and the like. The fluid impermeable covering 14 has a complex surface that comprises indentations or villi 18.

Figure 5A:
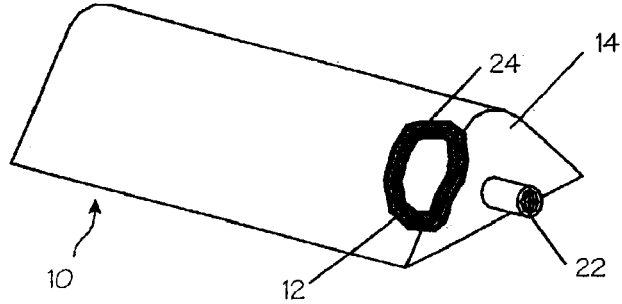
FIG. 5A illustrates an inflatable hemostatic packing device.

FIG. 5A illustrates yet another embodiment of the hemostatic, packing device 10 wherein the device may have fluid reversibly or irreversibly introduced to provide for size adjustment. The fluid impermeable covering 14 is, as in the previous figures, fluid impermeable. It is formed into a closed bladder with a shape adapted to fill typically voids in damaged organs and body parts. An access port 22 provides for fluid communication from the exterior of the packing device to the interior of the device, for introduction of substrate materials or materials to fill the substrate 12 within the outer layer. The packs may also be filled with water or oil, or by gas such as air, carbon dioxide, nitrogen and the like. In this embodiment, the substrate 12 is bladder formed from a fluid impermeable membrane that is filled with material to achieve the desired volume. The substrate 12 membrane is fabricated either from elastic materials such as silastic or polyurethane, or it is an inelastic bag with folds that allow for size increase. The outer surface of the substrate 12 preferably is not adhered in all places to the fluid impermeable covering 14 of said device 10 and optionally a lubricating layer 24 is placed between the two structures. The fluid impermeable covering 14 of said device 10 is fabricated from either elastic materials such as polyurethane or silicone rubber, or it is an inelastic material such as polyethylene terephthalate, polyimide, polypropylene or polyethylene or a copolymer including one of these materials. The fluid impermeable covering 14 of the hemostatic packing device 10 may be smooth, indented or include villi. The villi or indents may be macroscopic and have size ranges from 0.1 mm to 10 mm. The villi or indents may also be microscopic and difficult to see with the unaided eye. Such sizes are less than 0.1 mm.

Referring to FIG. 5A, the hemostatic packing device 10 comprises a hydrogel material that is placed into a wound and expands upon absorption of fluids from the patient to compress the wound. In this embodiment, the substrate 12 is fabricated from hydrophilic hydrogels such as those described by Park et al. and are incorporated herein by reference. Hydrogels are made from materials such as, but not limited to, carboxymethyl cellulose, cross-linked sodium starch glycolate, and cross-linked polyvinylpyrrolidone and the like. The substrate 12 can also be fabricated from a water-absorbable sponge that expands once it becomes wet. The water-absorbable sponge may be fabricated from materials such as, but not limited to polyvinyl alcohol, polymethyl cellulose, and the like. In this embodiment, the fluid impermeable covering 14 is provided with an opening to allow for fluid penetration into the substrate 12 to allow the expansion to occur. This opening may be the access port 22 and the fluid to expand the hydrogel or sponge may be injected through the access port 22. Alternatively, in the case of the hydrogel, the substrate 12 and the fluid impermeable covering 14 may be of the same hydrogel material. Hydrogels generally absorb water but do not adhere to biological surfaces. The hemostatic packing device 10 fabricated from hydrogel would be small enough in its dry state to be introduced through a laparoscopic access port and expand due to water absorption once placed within the body.

Figure 5B:
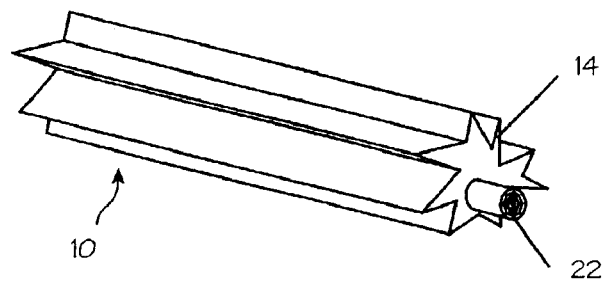
FIG. 5B illustrates one embodiment of the inflatable hemostatic packing device in its deflated or partially deflated state.

The devices of FIGS. 5A and 5B may be filled just prior to placement in the patient. The degree to which they are filled may be determined by the doctor or paramedic, depending on nature of the wound, including its size and organ which is wounded. The packs may also be filled or deflated after placement, whether to account for leakage or to adjust the size to account for changes in physiology or to make room for surgical devices. Such intraoperative filling of the bladder may be accomplished in an intraoperative time frame encompassing initial encounter and diagnosis of the patient, field treatment, emergency treatment and delayed treatment. The devices may also be placed perioperatively for a short period of recovery after surgery performed to repair the trauma.

Figure 6:
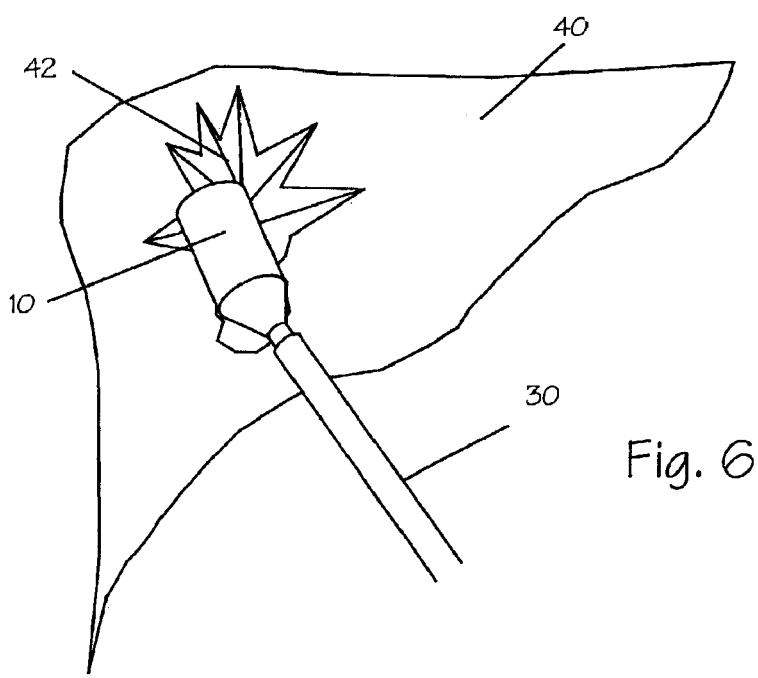
FIG. 6 illustrates a hemostatic packing device being introduced into a patient through a laparoscopic instrument.

FIG. 6 illustrates the hemostatic packing device 10 being introduced into a wound 42 in a liver 40 through a laparoscopic instrument 30. The laparoscopic instrument 30 is an axially elongate hollow device that provides porthole access to the internal organs of a patient.

FIG. 7 illustrates the hemostatic packing device 10 comprising an adhesive strip 28 on one side. The adhesive strip 28 is used to permit attachment of the hemostatic packing device 10 to other similar devices so as to create an impermeable syncytium or impermeable contiguous mass. The adhesive strip may also comprise an optional peel away cover that protects the adhesive strip 28 prior to use. The peel away cover is fabricated, preferably, from the same materials use to fabricate the fluid impermeable covering 14 of the hemostatic packing device 10. The adhesive strip is optionally fabricated from loop and hook fasteners such as Velcro® or even self-adhesive materials such as Coban®, marketed by 3M.

FIG. 8 illustrates another embodiment of the hemostatic packing device 10 further comprising a fluid impermeable drape 32 affixed to the packing device 10. The fluid impermeable drape 32 is, preferably adhered to the hemostatic packing device 10. The drape 32 comprises an adhesive layer 36 and a backing layer 38. The backing 38 is, preferably, fabricated from non-elastomeric materials such as, but not limited to, polyethylene, polypropylene, and the like. It is preferable that the drape 32 does not stretch once applied. The adhesive layer 36 is on the same side of the drape 32 to which the hemostatic packing device 10 is affixed. The hemostatic packing device 10 further optionally comprises a series of straps 34 to assist with fixation of the device to the patient. The straps 34 are fastened with standard buckles, Velcro or the like. This embodiment of the device 10 is useful for treatment of wounds to the periphery and especially those wounds that involve vascular injury. Such periphery includes the thigh, knee, lower leg, arm, shoulder, and forearm.

Figure 9A:
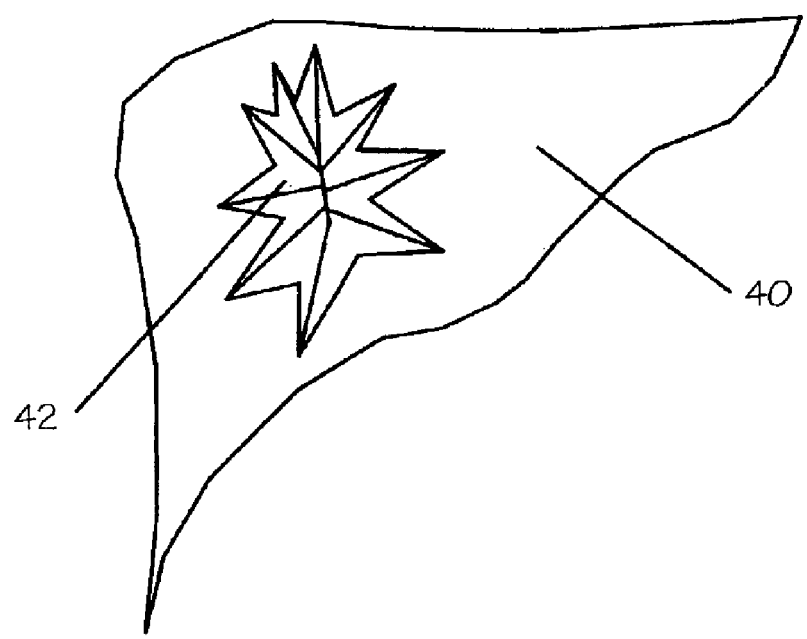
FIG. 9A illustrates a wound of the liver.

FIG. 9A illustrates the wound 42 to the liver 40. The liver 40 represents an exemplary case of parenchymal tissue that is friable and becomes severely damaged during an abdominal injury.

Figure 9B:
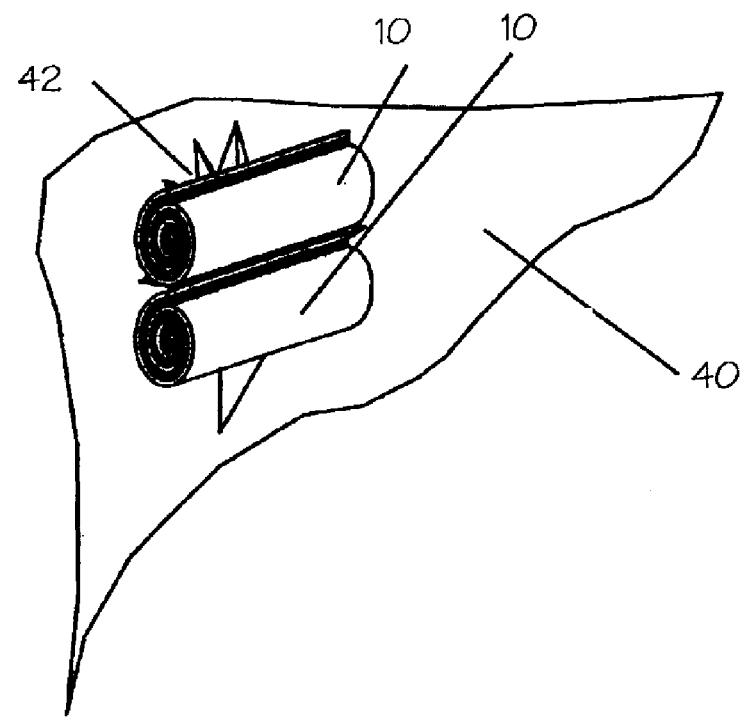
FIG. 9B illustrates the wound of the liver being treated by application of internal tamponade of hemorrhage with the impermeable hemostatic packing device used in a perihepatic location.

FIG. 9B illustrates the wound 42 to the liver 40 being treated by application of intra-parenchemal packing using one or more hemostatic packing devices 10. In this embodiment, two hemostatic packing devices 10 are used to provide hemostasis for the wound 42. The hemostatic packing devices 10 are applied manually via open surgery or laparoscopically, depending on the nature of the wound and the surgical technique, as determined by the doctor or paramedic placing the packs.

Figures 10A, 10B:
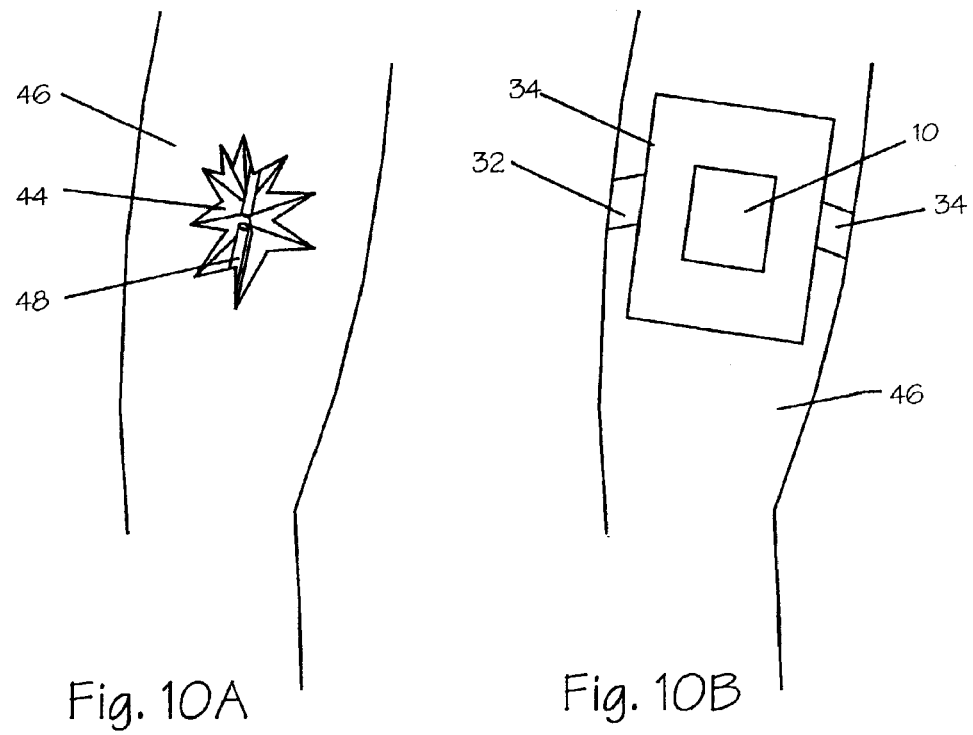
FIG. 10A illustrates a wound of an exemplary extremity, the thigh, with femoral artery transection.
FIG. 10B illustrates the wound to the thigh being treated by application of an impermeable hemostatic packing device with the adhesive impermeable drape.

FIG. 10A illustrates a wound 44 to the periphery and more specifically, the thigh 46. The wound 44 has caused femoral artery 48 to become transected.

FIG. 10B illustrates the wound 44 to the thigh 46 being treated by application of the impermeable hemostatic packing device 10 with the adhesive impermeable drape 32 and straps 34.

In yet another embodiment, a wound closure is fabricated from a material that has skin and wound contact surfaces that are impermeable to water, blood and tissue penetration. Preferably, these wound closure devices are fabricated from sheets of materials such as, but not limited to, polyurethane, polypropylene, polyethylene, silicone elastomer, and the like. The skin contact surface is a biocompatible adhesive and is further impregnated with anti-microbial agents such as, but not limited to, iodine, betadine and the like. The bandage or wound closure device is large enough to completely surround the wound and seal in the wound so that blood cannot escape. The bandage, optionally, has additional straps that fully surround the body or appendage and seal with Velcro, buckles, clamps or the like. The bandage or wound closure device seals the wound against the full systolic blood pressure and, thus tamponade any bleeding that occurs from damaged vessels other than the one repaired with the shunt 10. The bandage comprises an adhesive region that sticks to the skin, even if the skin is wet or bloody. The bandage is optionally maintained in place using straps that wrap around the body or appendage and secure the bandage in place with adequate pressure to generate pressure tamponade of the wound.

The preferred wound closure is a large piece of Ioban®, a trademark and product of 3M Corporation, the non-adhesive side of which is adhered to a piece of woven gauze or mesh to provide adequate structure to the weak membrane of the Ioban®. The Ioban has adhesive and anti-microbial properties preferred for this application. A strap extending from opposing ends of the bandage and terminated with a loop and hook fastener such as Velcro® or 3M Coban®, which is self-adherent, assists in maintaining pressure against the wound and proving full tamponade of the hemorrhage. In yet a further embodiment, the central part of the skin contact region comprises a malleable or conformable pad, preferably adhered to the wound closure device, which helps to exert hemostatic force on the wound. The conformable pad evenly distributes the forces throughout the wound so that no areas receive either too high a pressure, or too low a pressure, such as would permit further bleeding. The conformable central pad may be a block of foam covered by the aforementioned impermeable layer, or it may be an impermeable membrane, preferably elastomeric, filled with liquid such as saline or even a particulate material such as, but not limited to, sand, flour, sugar, silicone oil, or the like. In a preferred embodiment, the material used to form the fluid-tight membrane is liquid impermeable but gas permeable. Materials suitable for such permeability requirements include expanded polytetrafluoroethylene (ePTFE) and the like.

Figure 11:
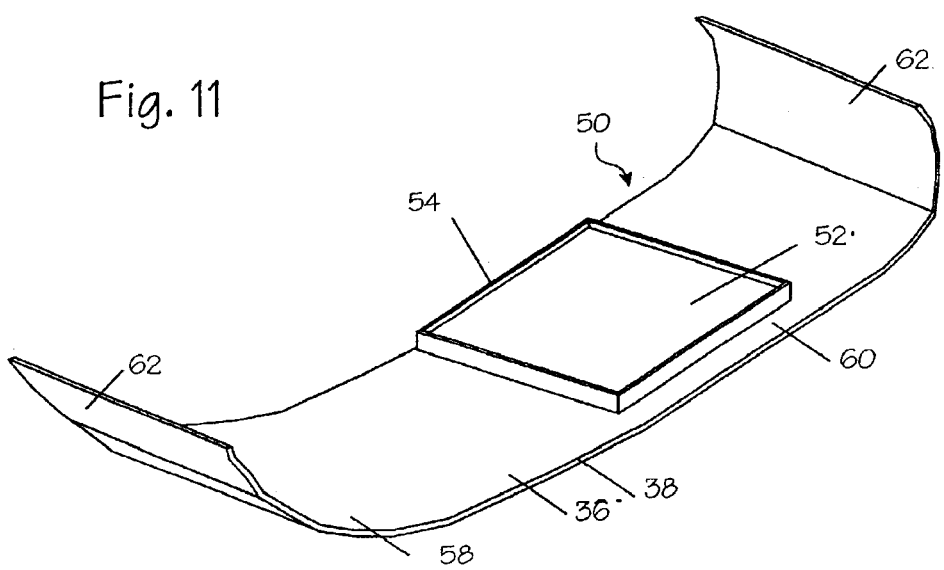
FIG. 11 illustrates a wound dressing or bandage comprising a blood dam, for treating a wound to the arm or the leg.

FIG. 11 illustrates a wound dressing or bandage comprising a blood dam, for treating a wound to the arm or the leg. The hemostatic packing device 10 is in the form of a wound dressing or bandage 50. The wound dressing or bandage 50 further comprises a gauze or absorbent region 52. The gauze or absorbent region 52 may have material bulked up or rolled up to aid in the application of pressure to cause pressure tamponade of the wound or perforation to the body. The gauze or absorbent region 52 may alternatively be a fluid pouch, which may be inflated or deflated to apply the required pressure tamponade to the wound area. The gauze or absorbent region 52 is further comprised of a peripheral gasket 54 or a plurality of gaskets 54 running in a honeycomb, rectangular or other appropriate pattern throughout and within the gauze or absorbent region 52 of the bandage 50. The gasket 54 aids in hemodynamic control and is made out of fluid impermeable materials, such as, but not limited to, silicone, C-flex, hydrogels, silicone oil-filled membrane, polyurethane closed-cell foam, and the like. The typical width of the gasket 54 material will be ⅛ to ¼ inch, but the gasket may be made larger for wounds that require greater hemodynamic stabilization which can be achieved by the damming function of a larger gasket. The gasket 54 is wide enough to distribute pressure over the skin area so as not to cause petcheciae, bruising or tissue damage while applying enough pressure to seal against systemic arterial pressure, typically 100 to 300 mm Hg. The dam or gasket 54 generally presses gently into the tissue surrounding the wound to ensure a strong resistance to hemorrhage or leakage of blood beyond the dam. Affixed or integral to the gauze or absorbent region 52 is a plurality of fluid impermeable straps 58 that will wrap around the extremity or wound area. The straps 58 may contain an adhesive layer 36 or may be of material suitable for stretch wrapping. Optionally, the straps 58 may comprise an adhesive layer 36 and a backing layer 38. The backing 38 is, preferably, fabricated from non-elastoineric materials such as, but not limited to, polyethylene, polypropylene, Tyvek®, polytetrafluoroethylene, polyester, and the like. Another option for the straps 58 could be adhesive straps 58 made from materials such as, but not limited to, those manufactured by 3M, Inc., under the trade name of Ioban. This material would be suitable and desirable for use as the straps 58 due to its chemical composition and inherent antiseptic properties. In addition, the wrapping material may also have buckles or Velcro 62 or another means of securing or attaching the bandage in place on the patient. Self-adhesive materials such as, but not limited to, those manufactured by 3M, Inc., under the trade name of Coban® are suitable for use as the binding system for the straps 58. The straps 58 may also be fluid impermeable, so as to aid in the wound containment. The bandage or wound dressing 50 also has a free end or side 60. Ideally, the wound dressing or bandage 50 would be packaged with a protective, removable layer over the gauze or absorbent region 52 and quite possibly over the entire surface applied to the patient.

FIG. 12 illustrates another embodiment device illustrated in FIG. 11. The hemostatic packing device 10 is in the form of a wound dressing or bandage 50, as shown in FIG. 11. The wound dressing or bandage 50 further comprises a gauze or absorbent region 52. The gauze or absorbent region 52 is further comprised of a plurality of dams or gaskets 54 running or weaving in a honeycomb, rectangular, diamond, or other appropriate pattern throughout and within the gauze or absorbent region 52 of the bandage 50. The gasket 54 aids in hemodynamic control and is made out of fluid impermeable materials, such as, but not limited to, silicone, C-flex, hydrogels, silicone oil-filled membrane, polyurethane closed-cell foam, and the like. The typical width of the gasket 54 material will be ⅛ to ¼ inch (again, the gasket may be made larger for wounds that require greater hemodynamic stabilization which can be achieved by the damming function of a larger gasket). The gasket 54 is wide enough to distribute pressure over the skin area so as not to cause petcheciae, bruising or tissue damage but enough pressure to seal against systemic arterial pressure, typically 100 to 300 mm Hg.

FIG. 13 illustrates a wound dressing with a blood dam as shown in FIGS. 11 and 12, modified with the addition of a valve communication from the intended body contacting surface to the intended exterior or superficial side of the wound dressing. The hemostatic packing device 10 is in the form of a wound dressing or bandage 50, similar to those shown in FIG. 11 of 12. The wound dressing or bandage 50 further comprises a gauze or absorbent region 52 and a valve 56. The valve 56, which resides within the gasket 54, may be used to remove fluids or add agents to assist in the coagulation or wound containment. The valve 56 may be, but is not limited to, a duck bill type of valve, or the like.

Figure 14A:
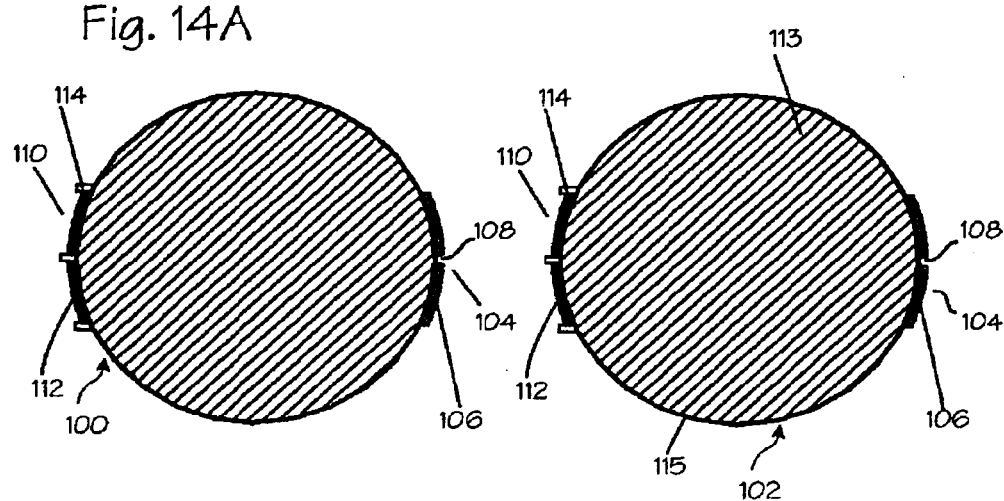

FIG. 14A illustrates a system of hemostatic packs which can be releasably attached together just prior to use to form a hemostatic structure as desired by the doctor treating a patient. Hemostatic packs 100 and 102 both comprise solid shapes (such as cylinders, prisms, pyramids, cones, spheres, polyhedrons and extended lengths with other cross-sections such as rectangular, oval, circular, trapezoidal, triangular, etc.), each with an impermeable outer layer 115 and a soft-conformable filler region 113. The left hand internal pack 100 further comprises a female adhesive region 104 further comprising an adhesive material 106 and a plurality of adhesive material gaps 108. The right hand internal pack 102 further comprises a male adhesive region 110 further comprising an adhesive material 112 and a plurality of dams 114. In the preferred embodiment each hemostatic pack has at least one male adhesive region 110 and one female adhesive region 104 so that a plurality of packs can be chained together to form a contiguous blood impermeable barrier. In the preferred embodiment, the adhesive material 106 is the hook style of Velcro® type hook and loop fastener while the adhesive material 112 is the tufted style of Velcro® fastener. Thus when the adhesive regions 106 and 112 are brought into contact, they adhere to each other. The adhesive regions 106 and 112 are reversibly adherent to each other and may be separated by manual force, if desired. In another embodiment, the adhesive regions 106 and 112 may be fabricated from materials such as 3M Coban® and the like, hydrogel adhesives and the like, and typical adhesives such as are used in medical bandages. Thus, the hemostatic packs are provided with releasable attachment means, and any other suitable releasable attachment means may be use in place of those illustrated. The adhesive material gaps 108, in the female adhesive region 104 are spaced and designed so that the dams 114 of the male adhesive region impinge on and seal against an impermeable surface of the female adhesive region 104. The adhesive material gaps 108 and the dams 114 may be configured in a straight line or they may be curved into a wavy pattern to improve the sealing area. Special guide markers either printed on the packs 100 and 102 or fabricated as raised or detented surfaces on the packs 100 and 102 facilitate alignment of the dams 114 and the adhesive material gaps 108.

Figure 14B:
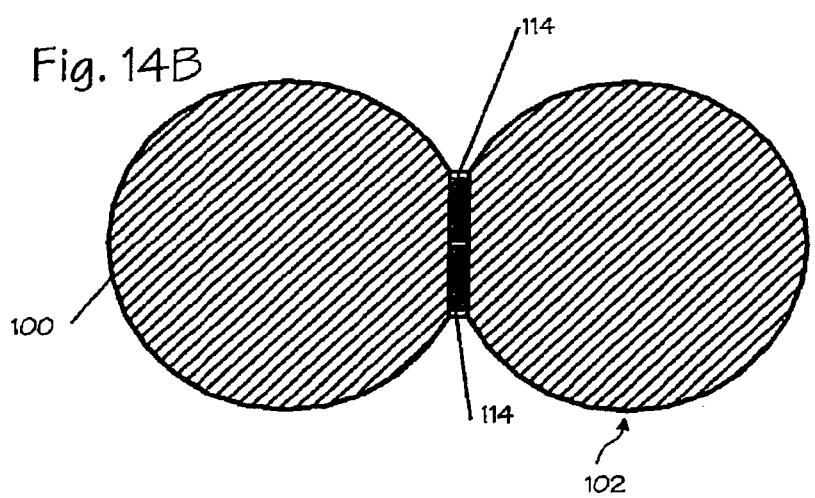
FIG. 14B illustrates a lateral sectional view of two internal hemostatic packs that have been joined together to form a syncytium wherein the barrier regions or dams render the adherent region impermeable to fluids such as blood.

FIG. 14B illustrates a cross-sectional view of the internal packs 100 and 102 following joining to form a continuous barrier pack. Referring to FIGS. 14A and 14B, the dams 114 seal against the impermeable surface 115 through adhesive material gaps 108. The adhesive regions 106 and 112 are firmly in contact and grip each other to hold the two packs 100 and 102 together without any area of seepage, leakage, or weeping. The dams 114 and the corresponding receiving gaps 108 serve to block any flow of fluid through the hook and loop fastening system (which may initially be somewhat permeable to blood), as well as to provide guides to help doctors assembling a gang of packs assemble them without substantial gaps between adjacent packs. For a typical use, such as internal organ packs (a ruptured liver, for example), the device can be provided in dimensions of about 3 to 4 inches long, about 0.5 to 2 inches in diameter, so that a doctor may assemble several packs into a gang to form a substantial wall to cover a large fracture.

In yet another embodiment of the barrier pack, the mating region between the two packs comprises adhesive regions such as those described for FIG. 14A, except that the barrier dams are replaced with fluid impermeable flaps that fold in to cover the adhesive regions following joining. One flap preferably covers each side of the adhesive region. In a preferred embodiment, the flaps cover the adhesive regions until they are needed to join with another barrier pack. At that time, the flap is pulled away, the two packs are joined, and the flap is folded in to cover the adhesive region and form a fluid-tight seal between the two barrier packs.

Referring to FIG. 1 through FIGS. 14A and 14B, the hemostatic packing device 10 is used to treat wounds that are typically caused by trauma. In a typical procedure, the surgeon or medic, using aseptic procedure, accesses the wound either by open surgery or laparoscopic surgery. The wound is irrigated and cleaned and excess fluids are removed by suction and blotting with gauze sponges. The surgeon may apply antiseptic agents or thrombogenic agents to the wound. The surgeon places the hemostatic packing device 10 into the wound and the device 10 is secured into place. Using current damage control procedure, it is preferable to stabilize the patient prior to removing the hemostatic packing device 10 and permanently repairing the wound. The hemostatic packing device 10 does not stick or heal into the wound and removal is not traumatic to the patient. The hemostatic packing device 10 is also well suited for a typical "sucking chest wound" because of its inherent impermeable properties. In this use, the one-way valve 56 permits fluid and air to exit the chest cavity but prohibits reflux of air into the chest cavity, a condition which prevents lung function and which is known as pneumothorax.

FIG. 15 illustrates a preferred embodiment of a wound dressing or bandage 120. The wound dressing or bandage 120 comprises a backbone 122 with a central region and two ends, a first fastener 126, a second fastener 128, a fluid-impermeable barrier 124, a fluid dam 132, a pillow pack 134, and an optional peripheral hemostatic region 130. The wound dressing or bandage 120 is configured to wrap around a body part, arm, leg, torso, head, etc. and fasten using the first fastener 126 and the second fastener 128. The fasteners 126 and 128 are of the type including, but not limited to, Velcro, buckles, snaps, jam cleats, buttons, and the like. An optional cinch mechanism to increase mechanical advantage and allow the caregiver to apply the bandage 120 with increased compression may be added to the configuration. The backbone 122 is preferably a woven fabric of material such as, but not limited to cotton, polyester, polypropylene, polyurethane, polyethylene, PTFE, nylon, and the like. The woven backbone is configured to be flexible but have high tensile strength, while porosity is not an important characteristic. The impermeable barrier 124 is preferably applied to the central region of the bandage 120 and is created by a separate polymer layer that is adhered or welded to the backbone 122. The backbone 122 may also be dipped, sprayed, or coated with materials such as, but not limited to, polyurethane, C-Flex thermoplastic, silicone elastomer, and the like. Since the dressing is intended for short-term application, gas permeability is not considered objectionable but it is desirable. The fluid dam 132 is fabricated from materials including those used to fabricate the fluid impermeable barrier 124. The fluid dam 132 may also be fabricated from gel-filled membranes, hydrogels, oil-filled membranes, and the like. The membrane of the fluid dam 132 is preferably, inelastic at the pressures used for filling. The fluid dam 132 is configured to provide a pressure seal against the body and form a complete barrier to prevent blood from escaping the wound. In another embodiment, the fluid dam 132 is inflatable following or before application to the patient through a valve such as a stopcock or standard inflation valve on the exterior surface of the bandage 120.

Further referring to FIG. 15, the pillow pack 134 is adhered to the central region of the bandage 120, preferably to the fluid impermeable region 124. The pillow pack 134, preferably resides within the region described by the fluid dam 132. The pillow pack 134 outer surface is preferably smooth and resistant to blood adherence but in another embodiment, the pillow pack 134 outer surface may be a fabric mesh or other convoluted surface capable of accelerating thrombosis or of carrying thrombogenic materials or antimicrobial agents. The pillow pack 134 is the primary distributor of force upon the wound to generate pressure tamponade. The pillow pack 134 is capable of extruding into a wound and distributing pressure evenly to generate hemostasis. The pillow pack 134 preferably comprises an elastomeric membrane filled with materials such as, but not limited to, air, water, oil, sand, gel materials, and the like. The pillow pack 134 in the embodiment where gas, air or liquid, is used for inflation, comprises an optional valve such as stopcock on the exterior surface of the bandage 120. The peripheral hemostasis region 130 preferably resides within the fluid dam 132 and accelerates clotting in the region outside the wound area but within the environs of the bandage 120. The peripheral hemostasis region 130 is fabricated from materials such as, but not limited to, cotton gauze, polyester knits and the like.

The present invention is suitable for wounds to many parts of the body. The external hemostatic pack works on the arms, the legs, the head, a finger, the torso, etc. The present invention also describes a band-aid type device with the further enhancement that a fluid-tight dam is comprised within the device to prevent blood loss out the side of the band-aid.

The present invention includes apparatus and methods for treating wounds. The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A device adapted for packing a wound and achieving hemostasis comprising:
   a three dimensional pack, said pack comprising a soft, pliable substrate at least partially covered with a fluid impermeable covering;
   a releasable attachment means adapted for releasably securing the pack to other packs; and
   anti-pathogenic agents disposed on the covering.

2. A device adapted for packing a wound and achieving hemostasis comprising:
   a three dimensional pack said pack comprising a soft, pliable substrate at least partially covered with a fluid impermeable covering;
   a releasable attachment means adapted for releasably securing the pack to other packs; and
   haemostatic agents disposed on the covering.

3. A device adapted for packing a wound and achieving hemostasis comprising:
   a three dimensional pack, said pack comprising a soft, pliable substrate at least partially covered with a fluid impermeable covering;
   a releasable attachment means adapted for releasably securing the pack to other packs; and
   a plurality of indentations filled with haemostatic agents.

4. A device adapted for packing a wound and achieving hemostasis comprising:
   a three dimensional pack, said pack comprising a soft, pliable substrate at least partially covered with a fluid impermeable covering;
   a releasable attachment means adapted for releasably securing the pack to other packs; and
   a plurality of indentations filled with anti-pathogenic agents.

5. The device of claim 1, 2, 3, or 4 wherein the device substrate comprises a water swellable hydrogel and a fluid permeable region on at least a portion of said outer surface of said device.

6. The device of claim 1, 2, 3, or 4 wherein the substrate comprises cotton gauze.

7. The device of claim 1, 2, 3, or 4 wherein said substrate comprises foam.

8. The device of claim 7 wherein said foam comprises polyurethane, polyvinyl chloride, polyethylene, polyvinyl acetate, silicone rubber, polyvinyl chloride, polymethyl methacrylate or a copolymer including one of these materials.

9. The device of claim 1, 2, 3, or 4 wherein said substrate comprises open-cell foam.

10. The device of claim 1, 2, 3, or 4 wherein said substrate comprises closed-cell foam.

11. The device of claim 1, 2, 3, or 4 wherein said substrate comprises silicone oil.

* * * * *